(12) United States Patent
Scaringe et al.

(10) Patent No.: US 9,050,360 B1
(45) Date of Patent: Jun. 9, 2015

(54) APPARATUS FOR CRANKCASE PRESSURE REGULATION USING ONLY AMBIENT AIR OR COOLANT TEMPERATURE

(76) Inventors: Robert P. Scaringe, Rockledge, FL (US); Gregory S. Cole, Melbourne, FL (US); Daniel Lambert, Merritt Island, FL (US); Daniel Staples, Orlando, FL (US)

( * ) Notice: Subject to any disclaimer, the term of this patent is extended or adjusted under 35 U.S.C. 154(b) by 888 days.

(21) Appl. No.: 12/978,723

(22) Filed: Dec. 27, 2010

(51) Int. Cl.
*F25D 17/06* (2006.01)
*A61K 48/00* (2006.01)

(52) U.S. Cl.
CPC ......... *A61K 48/00* (2013.01); *F25B 2313/0293* (2013.01); *F25B 2600/112* (2013.01)

(58) Field of Classification Search
CPC .................. F25B 2313/0293; F25B 2600/112
USPC ............. 62/89, 125, 126, 177, 178, 180, 181, 62/186, 183, 207, 204
See application file for complete search history.

(56) References Cited

U.S. PATENT DOCUMENTS

| | | | |
|---|---|---|---|
| 2,047,827 A * | 7/1936 | Lamb | 62/119 |
| 2,720,756 A * | 10/1955 | Stebbins | 62/160 |
| 3,505,828 A * | 4/1970 | Vander Molen et al. | 62/180 |
| 3,918,268 A * | 11/1975 | Nussbaum | 62/150 |
| 4,373,353 A * | 2/1983 | Anzalone | 62/200 |
| 4,617,804 A | 10/1986 | Fukushima et al. | |
| 4,688,392 A * | 8/1987 | Fujimoto et al. | 62/174 |
| 4,689,968 A | 9/1987 | McCulloch et al. | |
| 4,807,455 A | 2/1989 | Mauer | |
| 4,934,155 A * | 6/1990 | Lowes | 62/197 |
| 5,157,934 A | 10/1992 | Uchida | |
| 5,259,210 A | 11/1993 | Ohya et al. | |
| 5,419,146 A | 5/1995 | Sibik et al. | |
| 5,632,154 A | 5/1997 | Sibik et al. | |
| 5,749,238 A | 5/1998 | Schmidt | |
| 5,782,101 A | 7/1998 | Dennis | |
| 5,782,103 A | 7/1998 | Schmidt | |
| 5,809,794 A | 9/1998 | Sibik et al. | |

(Continued)

FOREIGN PATENT DOCUMENTS

GB 2345353 A * 7/2000

OTHER PUBLICATIONS

Sporlan Crankcase Pressure Regulating Valves, Sporlan Valve Company, Bulletin 90-10, Jan. 1989.

(Continued)

*Primary Examiner* — Jonathan Bradford (57) ABSTRACT

A vapor compression thermal control system having at least one electrically powered evaporator fan and an apparatus for preventing compressor overloading apparatus having a sensor that measures temperature of air entering the evaporator. That measured temperature is compared with at least one predetermined temperature setting to activate a predetermined evaporator blower on/off duty cycle when the measured temperature exceeds the predetermined temperature. Alternatively, the apparatus can have a sensor that measures temperature of air being used to cool the condenser, and that measured temperature is then compared with at least one predetermined temperature setting to activate a predetermined evaporator blower on/off duty cycle when the measured temperature exceeds the predetermined temperature. In either case, it is evaporator air flow that is modulated when the system is operated as a heat pump. For liquid cooled evaporators, however the circulation pump instead of the fan is modulated.

15 Claims, 4 Drawing Sheets

(56) References Cited

U.S. PATENT DOCUMENTS

| | | | |
|---|---|---|---|
| 6,018,959 | A | 2/2000 | Schmidt |
| 6,141,981 | A | 11/2000 | Reason et al. |
| 6,560,980 | B2 | 5/2003 | Gustafson et al. |
| 6,854,285 | B2 | 2/2005 | Jessen |
| 2007/0125105 | A1* | 6/2007 | Manole ........................ 62/180 |
| 2009/0151375 | A1* | 6/2009 | Tarr et al. .................... 62/180 |
| 2011/0265500 | A1* | 11/2011 | Black, Jr. et al. ............ 62/89 |

OTHER PUBLICATIONS

Sporlan Evaporator Pressure Regulating Valves, Sporlan Valve Company, Bulletin 90-20, Jan. 1989.

Sporlan Thermostatic Expansion Valves, Sporlan Valve Company, Bulletin 10-9, Aug. 2005.

* cited by examiner

APPARATUS FOR CRANKCASE PRESSURE REGULATION USING ONLY AMBIENT AIR OR COOLANT TEMPERATURE

BACKGROUND AND SUMMARY OF THE INVENTION

The present invention relates to a crankcase pressure regulator and, more particularly, to crankcase pressure regulation using airside heat transfer in the evaporator of a vapor-compression cooling system and the like.

As is well known in the relevant art, the basic vapor compression cooling or refrigeration system consists of a compressor, condenser, evaporator, and expansion (throttling) valve (typically a Thermal Expansion Valve, Capillary Tube, or Orifice Plate). In these systems, refrigerant is evaporated at low pressure to provide cooling and then this low-pressure vapor is then compressed by the compressor and condensed in the condenser, with heat being rejected at the higher condensation temperature. The condensed refrigerant is then throttled back to low pressure, to enter the evaporator and repeat the process.

Actual air conditioners, refrigeration systems and the like typically utilize other components in addition to these basic items, such as oil separators, suction-line (liquid) accumulators, liquid receivers, mufflers, recuperative heat exchangers, reversing valves, high pressure and low pressure safety switches, thermal overload protection, and filter-driers. The construction of and reasons for using these components are also well known in the art.

Essentially during startup or lower than design temperature lift, the capacity of the vapor-compression system increases dramatically causing the compressor to overload (capacity increases with decreased lift, i.e., the temperature difference between the condenser and evaporator). Therefore, in addition to the other components in a vapor compression cooling system, a crankcase pressure regulator is a common accessory that is added to many systems to prevent the compressor's motor from being overloaded when the pressure of the refrigerant supplied to the inlet of the compressor (the compressor suction side pressure) rises above the design pressure. As the inlet pressure to the compressor increases above the design pressure, a regulator is commonly employed (between the evaporator outlet and compressor inlet) to drop the pressure between the evaporator outlet and the compressor inlet.

Since the compressor crankcase is typically operated at the suction-side pressure, the above-mentioned valve is commonly referred to as a crankcase pressure regulator. These regulator devices are well know and commercially available (see, e.g., Sporlan Valve Company Bulletin 90-10, (January 1989). These regulator valves are also referred to as CRO valves, since their operation is to close on rise of the outlet pressure, i.e., they close on the rise of the compressor inlet pressure (the outlet of the CRO being connected to the compressor inlet) to regulate the compressor inlet pressure below a predetermined maximum pressure and thereby avoid compressor overloading.

Similarly, there is also another pressure regulating valve, that can be located between the evaporator outlet and the compressor inlet, known as an Evaporator Pressure Regulating valve to directly regulate evaporator, not compressor inlet, pressure. Such valves operate mechanically like a crankcase pressure regulating valve; however they control the pressure at the evaporator outlet rather than the compressor inlet. That, is rather than controlling the pressure at the regulating valve outlet (like a CRO), they control the pressure at the regulating valve inlet and are referred to ORI valves, since they open on rise of inlet pressure (or ORI). The performance of ORI valves is described in Sporlan Valve Company Bulletin 90-20 (January 1989). While the crankcase pressure regulators are designed to prevent compressor overloading, the ORI pressure regulating valves are used to keep the evaporator temperature from becoming too warm during operation at high evaporator heat loads, but do nothing to reduce compressor overloading (because at high evaporator temperatures they are fully open and provide no reduction in refrigerant flow).

The above-described crankcase pressure regulators are commonly spring activated mechanical pressure regulators. It is also possible, to utilize electrically actuated refrigerant valves controlled by the compressor inlet pressure to replace a CRO valve or controlled by the evaporator outlet pressure in the case of an ORI valve.

Another known method of maintaining the compressors suction line pressure from rising too much is to use a maximum operating pressure (MOP) thermal expansion valve (TXV), described at page 6 of Sporlan Valve Company Bulletin 10-9 (August 2005). The MOP TXV serves as another way to prevent compressor motor overloading. The MOP feature of the TXV causes the TXV to close above a predetermined evaporator pressure. By closing the TXV, the supply of refrigerant to the compressor is restricted, causing the suction line pressure to drop. Variations of this approach include the one described in U.S. Pat. No. 6,854,285, in which electrical feedback rather than fluidic feedback is used to control the expansion valve to maintain superheat and suction side pressure. Other feedback expansion device controllers are described in U.S. Pat. Nos. 5,782,103; 5,749,238; 6,018,959; 4,689,968; 5,809,794; 4,807,455; 4,617,804; 5,157,934; 5,259,210; 5,419,146; 5,632,154.

U.S. Pat. No. 6,141,981 discloses another microprocessor control of the expansion device to limit the mass flow rate of refrigerant through the compressor and avoid compressor overloading. More specifically, the compressor current draw, rather than a suction pressure or mass flow rate, is employed to adjust the refrigerant flow rate, by electrically adjusting the throttling valve. It is also well known to monitor compressor current draw and to turn the compressor off to avoid compressor overload, but such an approach eliminates all cooling or refrigeration effect.

While the above-described systems provide a way to control the mass flow rate of refrigerant to the compressor inlet, they are either additional mechanical devices or complex electronic devices. In addition while the spring actuated or electrical crankcase pressure regulator can be adjusted for a specific application, the MOP TVX cannot be field adjusted, and this lack of adjustability severely limits its flexibility.

Other devices to control vapor-compression systems include pressure switches or pressure monitoring devices that deactivate the compressor if the compressor discharge pressure is excessive. Likewise, using the relationship between a refrigerants saturation pressure and saturation temperature, the compressor could also be deactivated at a predetermined condenser refrigerant temperature.

U.S. Pat. No. 6,560,980 discloses a method and apparatus for controlling continuously-variable speed fans in both the evaporator and condenser fans of a refrigeration system to minimize the power consumed by the compressor and to minimize the unwanted heat added to the conditioned space due to the inefficiency of the evaporator fan. It includes providing a desired temperature for a conditioned space, measuring temperature at the inlet to the evaporator, and measuring temperature at the outlet to the evaporator. The method also includes calculating an actual temperature differential and adjusting evaporator fan speed based on the desired temperature differential and the actual temperature differential. This system is not designed to prevent compressor overloading but rather to maximize performance, by reducing heat added to the conditioned space by the fan and by reducing fan power consumption.

U.S. Pat. No. 5,782,101 discloses a device that prevents compressor overloading of a heat pump operating in heating mode, by cycling on/off or changing the speed of the evaporator fan, based on the pressure of the refrigerant at the compressor discharge rather than at the compressor inlet (crankcase pressure regulation usually controls the compressor inlet). The compressor inlet and outlet pressures are of course related, since a rise in the inlet pressure results in a rise in the outlet pressure, but they are typically not linearly related so a specific rise in the inlet pressure, will typically not create the same rise in outlet pressure. This patent also mentions that the refrigerant temperature instead of refrigerant pressure can be used. However, the compressor discharge temperature is determined from the compressor inlet enthalpy (inlet temperature and pressure), compressor discharge pressure and the work performed on the refrigerant by the compressor. Furthermore, the compressor inlet temperature is determined from the compressor inlet pressure and inlet enthalpy, with the evaporator design, evaporator temperature and evaporator superheat playing a role in the inlet enthalpy to the compressor. We also note that the compressor discharge temperature is not directly related to the ambient air temperature that is entering the evaporator, and FIG. 2 of the patent shows the pressure sensor 104 connected into the heat pump circuit directly after the compressor discharge 102 of compressor 101 and before the reversing valve 105.

We also consider it important to note that for a saturated refrigerant, the saturation pressure (evaporating or condensing refrigerant pressure) is directly related to saturation temperature, and therefore a refrigerant evaporating temperature (or refrigerant condensing temperature) can be substituted as the control variable instead of the refrigerant saturation pressure. However, the refrigerant entering or exiting the compressor is superheated, therefore the temperature of the refrigerant entering or exiting the compressor is not directly related to the pressure at these points, but is instead an independent variable as is well known.

Our invention proposes here to use the ambient air temperature (that enters the evaporator) and not any of the refrigerant pressures or refrigerant temperatures used by known devices. Thereby, we have developed an alternative method to control the suction line pressure and avoid compressor overloading so that complex mechanical or electronic devices are eliminated. Rather than add an additional device to actively control the flow of refrigerant and thus control the suction line pressure, we have recognized that the airside or, alternatively, water side heat transfer in the evaporator can be controlled to control the flow rate of evaporated refrigerant and therefore to control the suction side pressure.

In the case of airside heat transfer, there are alternative control methods such as the use of dampers to mask off a portion of the evaporator surface area, or even using a refrigerant bypass that short circuits portions of the evaporator to reduce the effective surface area of the evaporator. However, the currently preferred and simplest method is to modulate the speed or cycle (on/off) the evaporator blower. Modulating the speed of the fin, though feasible, is more complicated and costly than simply turning the fan on and off to adjust the average flow. Because of the thermal mass of the evaporator and the refrigerant contained in the evaporator, cycling the fan is just as effective, while being much simpler and less expensive to implement. Cycling the blower (on and off) will modulate the average heat transfer. While the compressor suction line pressure or the compressor current draw could be used to adjust the blower speed or to modulate the blower on and off to provide a lower effective heat transfer, we have discovered a better method of feedback control that is simpler, less expensive, and more reliable. We have discovered a method that has superior performance in actual operation and costs much less to implement, since air temperature measurement devices (such are thermistors, thermocouples, RTDs and the like) are much less expensive than refrigerant temperature sensors, refrigerant pressure sensors, or current sensors, and in many cases are already present in the system for temperature control or temperature monitoring. Also, they have the advantage over commonly used pressure sensors which are subject to drift and this requires frequent recalibration.

In the case of waterside heat transfer, the control can be, for example, a water bypass or a refrigerant bypass like that used in airside heat transfer described above. The simplest method is to modulate the speed or cycle (on/off) of an evaporator circulation pump/electric motor arrangement. Cycling in the case of a waterside heat transfer produces similar benefits as those described above for the airside transfer.

We have thus discovered that the ambient air temperature of the conditioned space, i.e., the temperature of the air entering the evaporator, can be used control the on/off operation (or fan speed) of the evaporator fan and still provide the compressor overload and crankcase pressure regulation function.

We have also discovered that if the temperature of the air entering the evaporator is not practical to monitor, then the temperature of the air entering the condenser can be used control the on/off operation (or fan speed) of the evaporator fan and provide the compressor overload and crankcase pressure regulation function.

We have also discovered that systems which use another type of suction side pressure regulation, such as the above-described embodiment a MOP TXV or crankcase pressure regulator can further benefit from the proposed evaporator blower cycling based on evaporator inlet air temperature (or condenser air inlet temperature), because our invention allows a multi-step control algorithm to be employed instead of simply regulating the crankcase pressure to below a single maximum suction side pressure. In fact a continuous change to the evaporator blower on/off duty cycle with temperature (continuous function) can be used instead of multiple step changes. In addition, the MOP TXV is pre-configured for a single maximum operating pressure and typically only available at two preset values. Also, the MOP TXV is not field adjustable, whereas our invention advantageously needs only a simple programming change in a control device to allow a different crankcase maximum operating condition to be easily implemented. The control device could even be programmed to learn and update the behavior, avoiding the need for manual programming changes.

BRIEF DESCRIPTION OF THE DRAWINGS

Other objects, advantages and novel features of the present invention will become apparent from the following detailed description when considered in conjunction with the accompanying drawings herein.

DETAILED DESCRIPTION OF THE DRAWINGS

Figure 1:
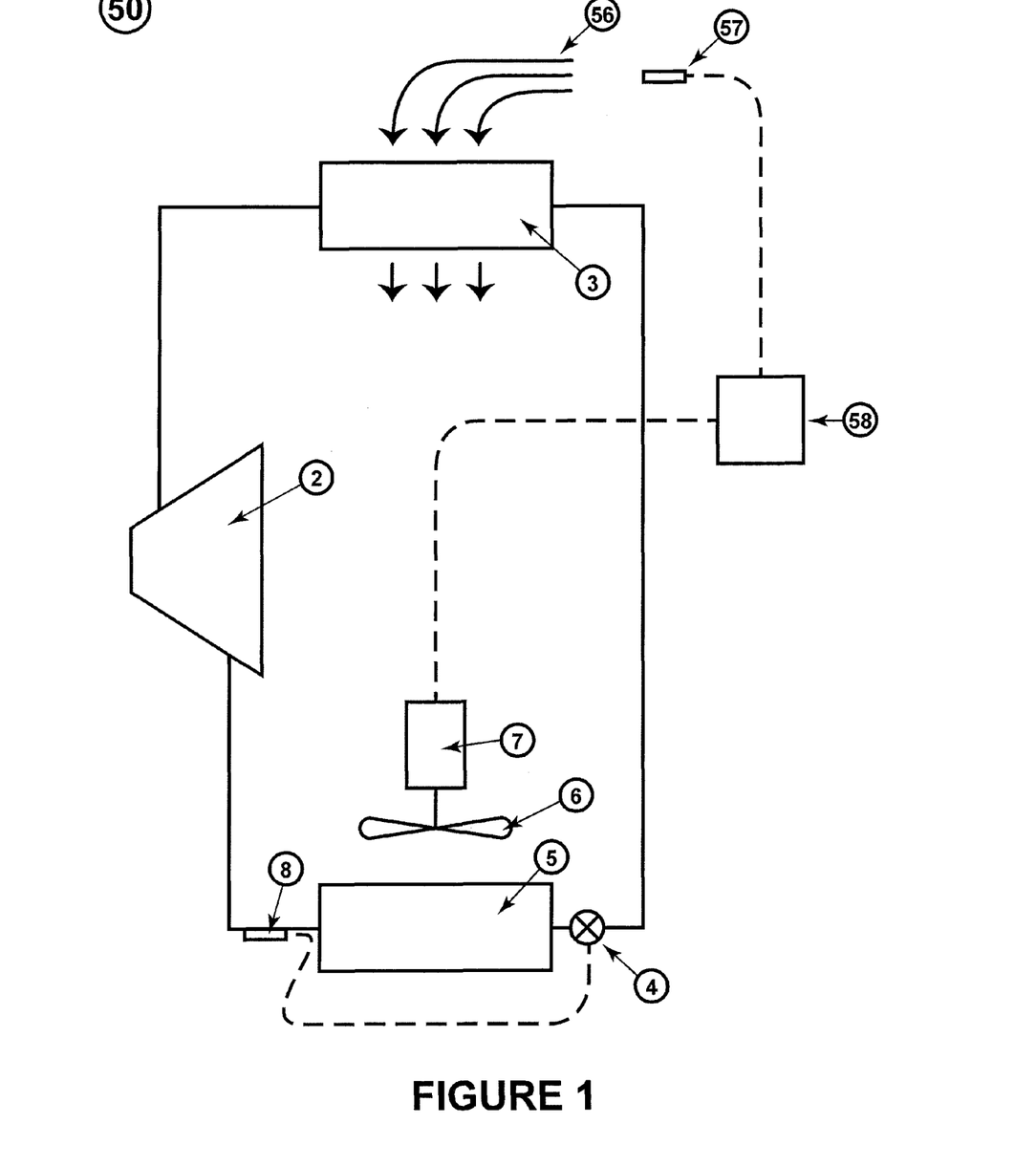
FIG. 1 is a schematic diagram of a known basic vapor compression system where the present invention is employed to prevent compressor overloading and crankcase pressure regulation, by obtaining the control feedback from the temperature of the air entering the condenser.

The vapor compression system is of a generally known type in that it includes a compressor 2, a condenser 3, a thermal expansion device (TXV) 4, an evaporator 5, and a temperature sensor 8 at the outlet of the evaporator 5 for regulating the TXV 4 shown in FIG. 1. However, no connection to the refrigerant circuit is necessary. Instead the temperature of the outdoor ambient air 56 (for an air-conditioner or refrigerator), determined by a sensor 57, i.e., the temperature of the air that normally would be available to cool the condenser 3, is configured to modify the blower duty cycle (activate or deactivate the evaporator blower), by supplying power to the motor 7 for an air mover 6 such as blower or fan. The controller or processor 58 evaluates the measured temperature of the air entering the condenser 3 (the air being shown in the arrows 56), and determines if a on/off duty cycle (and duration of the off and on periods) or a continuous ON cycle should be employed, on the fan motor when it is otherwise normally powered on.

Other control functions within the system shown in FIG. 1, such as a thermostat, are used to determine if the compressor 2, evaporator blower 6 and condenser fan (not shown) should be operating to supply cooling or refrigeration. The outdoor ambient temperature sensor 57 can be a bi-metallic member, (e.g. strip), a thermocouple, a resistance temperature transducer and a thermistor or the like and, together with the controller 58, function to determine if, when the blower is activated, it should operate continuously or operated on something less than a continuous duty cycle. With the use of a bimetallic device, the controller configuration can be simplified in that the latters' functionality is limited to turning the motor 7 on and off in response to the signal from the bimetallic device. Of course, it would also be within the skill in the art to combine the blower duty cycle control functions and thermostat control functions into a single controller or processor rather than use two separate controllers or microprocessors. In either case, the feedback control decision, to modify the evaporator duty cycle is the temperature of the air that would normally be entering the condenser, to cool the condenser, (the outdoor ambient air temperature in the case of air conditioning or refrigeration) as measured by a temperature sensor 57. It is noted here that for a heat pump operating in heating mode, the air entering the condenser is actually the indoor air.

Figure 2:
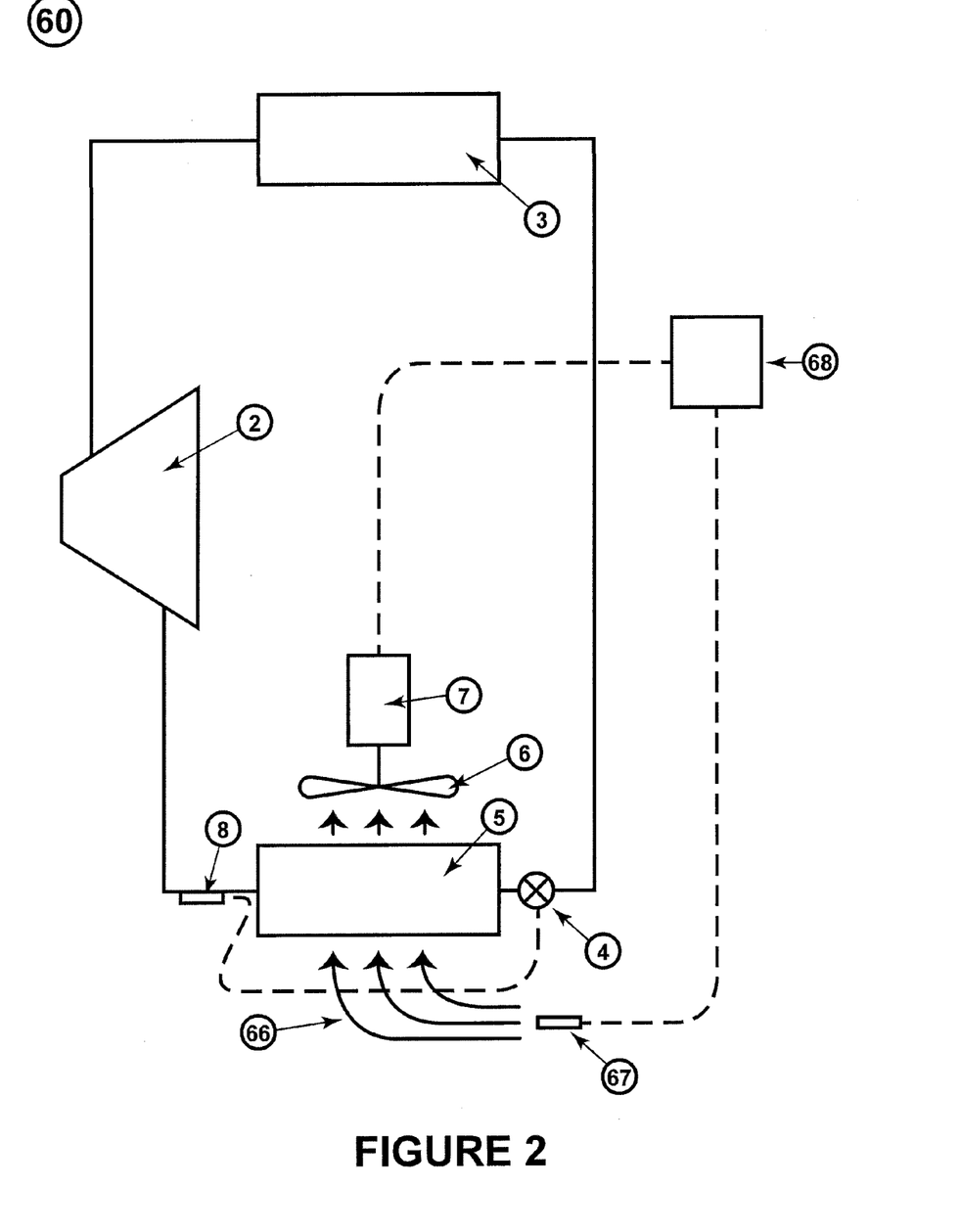
FIG. 2 is a schematic diagram of a currently preferred embodiment of the present invention, where the known basic vapor compression system has been modified to prevent compressor overloading and crankcase pressure regulation, by obtaining the control feedback from the temperature of the air entering the evaporator instead of the condenser.

FIG. 2 shows our electrical crankcase pressure and compressor overload regulation installed into the known basic system, and represents a currently preferred embodiment. Like the system of FIG. 1, with the same numerals identifying similar components, the FIG. 2 embodiment avoids the need for a connection to the refrigerant circuit. Here, however, the temperature of the air that flows over the evaporator 5 (as shown by the arrows 66) that is available to flow into and be cooled by the evaporator 5, is measured by sensor 67 and used to modify the blower duty cycle (activate or deactivate the evaporator blower) by supplying power to the blower motor 7. The controller or processor 68, evaluates the ambient temperature recorded by temperature sensor 67, and determines if an on/off duty cycle (and duration of the off and on periods) or a continuous ON cycle should be employed, on the fan motor when it is normally powered on otherwise. Other control functions within the system, such as a thermostat are used to determine if the compressor 2, evaporator blower 6 and condenser fan (not shown) should be operating to supply cooling or refrigeration.

The function of the temperature sensor 67 and controller 68 is to determine if, when the blower is activated by other means such in response to a thermostatic setting, it should operate continuously or operated on something less than continuous duty cycle. Again, it would be well within the skill of those in the art to combine the blower duty cycle control functions and thermostat control functions into a single controller or processor, rather than use two separate controllers or microprocessors. In either case, the feedback control decision, to modify the evaporator duty cycle is temperature of the air that is entering the evaporator as measured by a temperature sensor 67. Once again, it is also important to note that for a heat pump operating in heating mode, the air entering the evaporator is actually the outdoor air.

While the preferred sensor location to provide feedback for the fan modulation on and off is the temperature of the air entering the evaporator, which is the indoor air temperature in the case of a heat pump operating in cooling mode, the realization that either temperature can be used now allows that a single temperature sensor to be used for heat pump applications where the unit can be set to cooling or heating mode. For example, by placing the temperature sensor in the indoor air stream that enters the indoor heat exchanger (evaporator in cooling mode, condenser in heating mode), that sensor will monitors the evaporator inlet air temperature when the heat pump is set in cooling mode (FIG. 2) and monitor the condenser inlet air temperature (FIG. 1) when the heat pump is set in heating mode. The fan that should be modulated on and off must be the evaporator in either case, i.e., in a cooling mode it is the indoor fan and in a heating mode it is the outdoor fan. Likewise, by placing the temperature sensor in the outdoor air stream that enters the outdoor heat exchanger (the condenser in cooling mode and the evaporator in heating mode), that sensor will monitor the condenser inlet air temperature when the heat pump is set in cooling mode and monitor the evaporator inlet air temperature when the heat pump is set in heating mode.

EXAMPLE 1

On one air conditioning system that we developed, namely a 9,000 BTU/hr R-410 vapor compression system with a MOP TXV, the compressor became overloaded when operating at either high indoor temperatures or high outdoor temperatures, even though a MOP TXV had been utilized to keep the maximum crankcase pressure from exceeding 210 psig. This system could not operate at indoor or outdoor temperatures above 115° F. and would require a much larger space to accommodate a conventional mechanical crankcase pressure regulator. Therefore, an on-off fan control was installed to modulate the heat transfer, and the temperature of the air entering the evaporator was used as the feedback control temperature. The evaporator duty cycle algorithm for controlling the air conditioner was as follows:

When the temperature of the air entering the evaporator is Below 110° F. operate the evaporator blower as normal, that is the evaporator blower it is always on (operating at full capability) whenever both the system compressor and condenser fan are operating.

When the temperature of the air entering the evaporator is at or above 110° F. but less than 120° F., cycle the evaporator blower on for 10 seconds and off for 20 seconds, whenever both the compressor and condenser fan are operating.

When the temperature of the air entering the evaporator is at or above 120° F., cycle the evaporator blower on for 5 seconds and off for 20 seconds, whenever both the compressor and condenser fan are operating. Instead of a step change in the control function, a continuous function could be used. For this case, the continuous control would be as follows:

When the temperature of the air entering the evaporator is Below 110° F. operate the evaporator blower as normal, that is the evaporator blower it is always on (operating at full capability) whenever both the system compressor and condenser fan are operating.

When the temperature of the air entering the evaporator is at 110° F., cycle the evaporator blower on for 10 seconds and off for 20 seconds, whenever both the compressor and condenser fan are operating. As the evaporator air entering temperature increases above 110° F., decrease the evaporator blower on period by 1 second, for every 2° F., above 110° F. When the temperature of the air entering the evaporator reaches 120° F. and for temperatures above 120° F., cycle the evaporator blower on for 5 seconds and off for 20 seconds, whenever both the compressor and condenser fan are operating.

Our preferred embodiment is to use the step change rather than continuous function to control the evaporator blower duty cycle since it is a lower cost approach.

The evaporator fan modulating duty cycle and event temperatures (where this duty cycle is initiated) can be determined theoretically with conventional system modeling techniques or experimentally. If an experimental approach is used, one method we have found to be effective is to place the unit in an environmental chamber (both the evaporator and condenser are at the same temperature in the chamber) and increase the chamber temperature until the compressor is overloaded, typically determined by excessive compressor current draw. At this point, the temperature is lowered until a stable operating point below this overload temperature is determined. This defines an event temperature. The temperature in the chamber is then increased further until the overload condition is reached again. The evaporator fan is then modulated (turned on and off) to establish the fan on-off period and prevent compressor overloading. The first event temperature and evaporator fan duty cycle have now been determined. These setting are used on the unit and with the unit modulating the fan at these settings, the environmental chamber temperature is now further increased until the next compressor overload temperature is reached, at which point the process is repeated to determine a second event temperature and a second on-off duty cycle for the evaporator fan. This process can be repeated as needed to establish as many event temperatures and additional duty cycles as needed for the unit to operate over the anticipated operating temperature range.

By implement this electronic crankcase pressure regulation method, the same air conditioning unit that previously could not operate at temperatures above 115° F. (either indoor conditioned air temperature during start up or outdoor ambient temperature), was now able to achieve operating temperatures as high as 130° F. (either indoor conditioned air temperature during start up or outdoor ambient temperature).

EXAMPLE 2

In another air conditioning system that we developed, namely a 18,000 BTU/hr R-410 vapor compression system again with a MOP TXV, the compressor became overloaded when operating at either high indoor temperatures or high outdoor temperatures above 120° F., despite the presence of a MOP TXV to keep the maximum crankcase pressure from exceeding 210 psig. And this system also did not have the space inside the unit to utilize conventional crankcase pressure regulator. Therefore, the present invention of an on-off evaporator blower control was incorporated with monitoring the temperature of the air entering the evaporator as the feedback control temperature. The evaporator duty cycle algorithm for controlling the air conditioner was as follows:

When the temperature of the air entering the evaporator is Below 110° F. operate the evaporator blower as normal, that is the evaporator blower it is always on (operating at full capability) whenever both the system compressor and condenser fan are operating.

When the temperature of the air entering the evaporator is at or above 110° F. but less than 120° F., cycle the evaporator blower on for 10 seconds and off for 20 seconds, whenever both the compressor and condenser fan are operating.

When the temperature of the air entering the evaporator is at or above 120° F. but less than 130° F., cycle the evaporator blower on for 15 seconds and off for 45 seconds, whenever both the compressor and condenser fan are operating.

When the temperature of the air entering the evaporator is at or above 130° F., cycle the evaporator blower on for 10 seconds and off for 40 seconds, whenever both the compressor and condenser fan are operating.

By implement this electronic crankcase pressure regulation method, the same air conditioning unit that previously could not operate at temperatures above 120° F. (either indoor conditioned air temperature during start up or outdoor ambient temperature), was now able to achieve operating temperatures above 130° F. (either indoor conditioned air temperature during start up or outdoor ambient temperature).

For both these examples, our maximum operating temperature envelop was achieved, demonstrating that the electrical crankcase modulation was a simple and effective low-cost means to provide the extended operating temperature range.

When determining the ON/OFF duty cycle, the ratio of blower on time to blower off time is determined (analytically or experimentally) to avoid compressor unloading, but the characteristics and rotational inertia of the evaporator blower must also be included to determine the duration of the both on and off cycles. Ideally once the ratio of on time to off time is known, say 20% ON (5 seconds on, 20 seconds off) in Example 1, when air entering the evaporator is above 120° F., the on and off cycles should be as short as possible, to better approximate an average air flow rate. However, other factors must be considered. For example, the speed for the blower to spin up and spin down must be considered. In Example 2, the blower for the 18,000 BTU/Hr system was a different configuration in that it was larger and had more rotational inertia than that in Example 1. Therefore, the ON/OFF cycle time for the 20% duty cycle of this unit was set to 10 seconds on and 40 seconds off, instead of 5 seconds on and 20 seconds off. This was necessary because of the additional time for this blower to spin up and down. The overall life of the relay (that will be controlling the blower cycling) can also be a factor. In the designs of Examples 1 and 2, an electronic relay with essentially unlimited life was used. If a mechanical relay is used to control the on off operation of the fan, however, it is understood that the cycle duration should be increased to extend the life of the relay.

Figure 3:
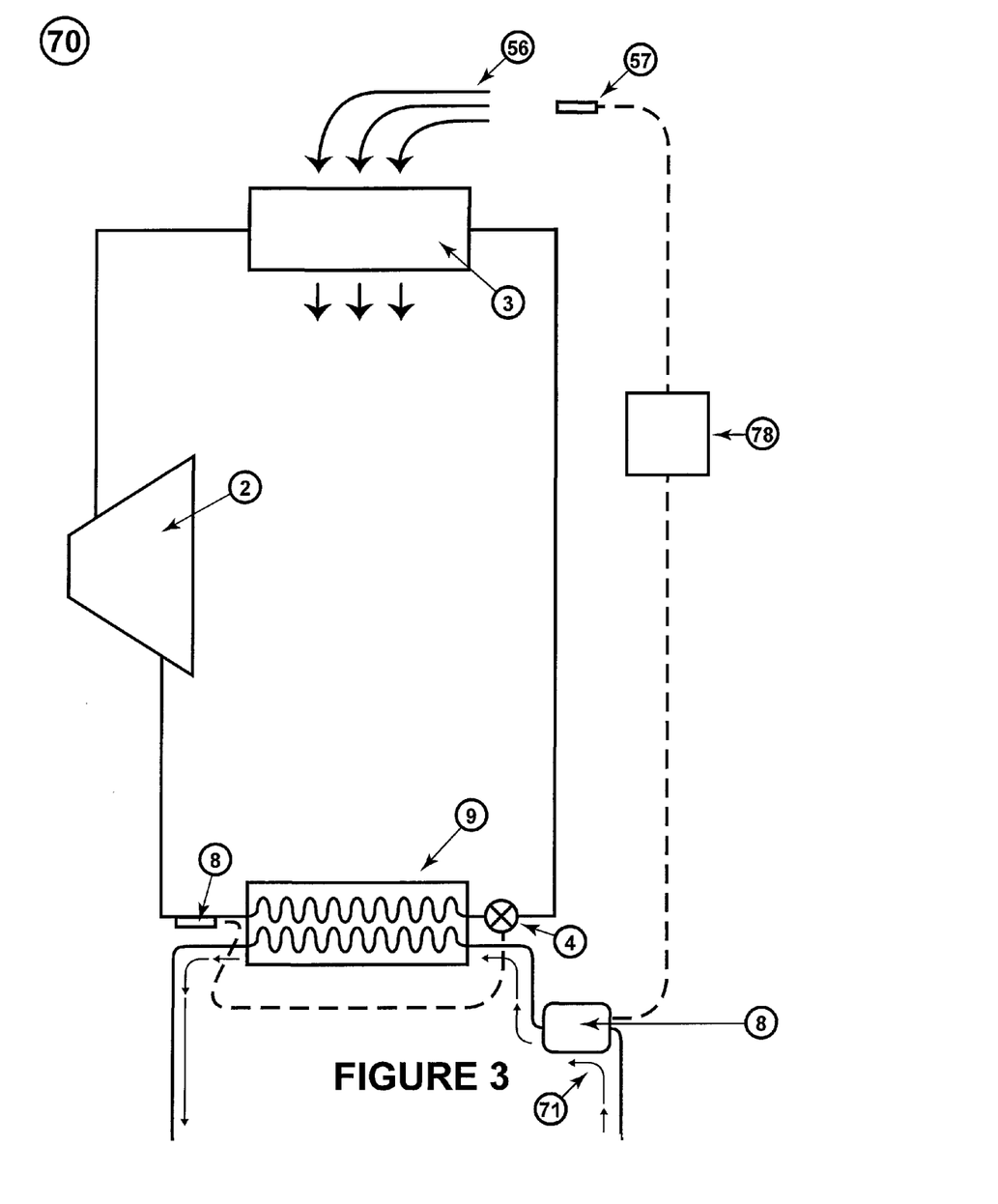
FIG. 3 is a schematic diagram of another embodiment of a known vapor compression system in which the evaporator is cooling a liquid (e.g. water) flow instead of an air flow as in the embodiments of FIGS. 1 and 2 and in which the temperature of the air entering the condenser is measured.
Figure 4:
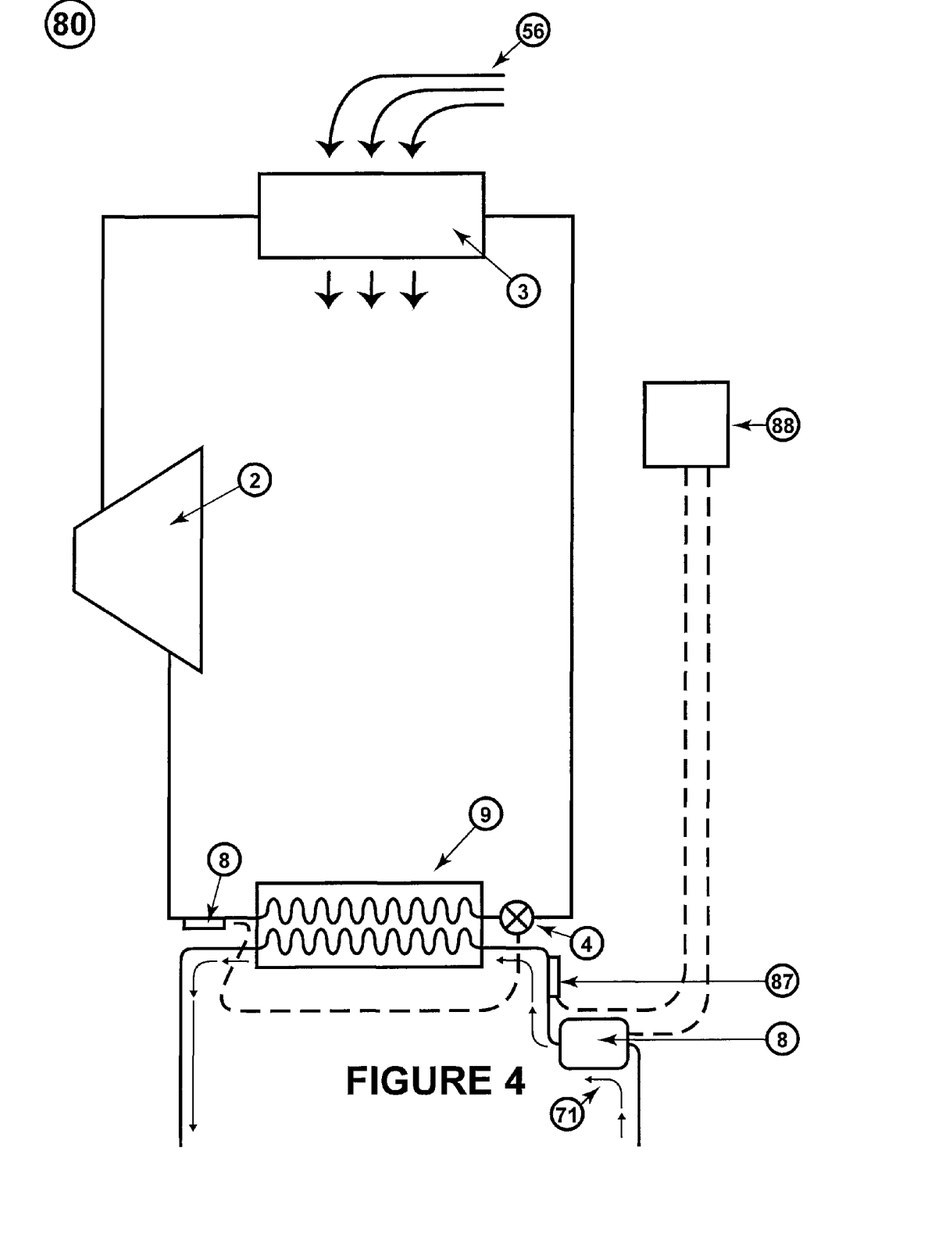
FIG. 4 is a schematic diagram of another version of a vapor compression system similar to that of FIG. 3 in which the temperature of the coolant entering the evaporator is measured instead of the air entering the condenser.

For air conditioning or refrigeration systems where the evaporator is cooling a liquid flow rather than an air flow such as shown in FIGS. 3 and 4 (where components identical to those used in FIGS. 1 and 3 bear the same numerals), the same principles apply, in this case, however, to reduce the heat transfer in the evaporator the coolant pump (controlling the liquid flow) rather than the evaporator blower is modulated on and off. The increased thermal mass (increased heat capacity) of the coolant liquid, compared to the air will mean longer on and off cycles can be used, and of course care must be taken to avoid freezing of the liquid cooling. Once again, the temperature of the air (or other fluid cooling the condenser) entering the condenser or the temperature of the liquid entering the evaporator can be the feedback control temperature.

In the system shown in FIG. 3, numeral 9 schematically represents an evaporator for cooling a liquid, in which a pump/electric motor arrangement 8 circulates through the liquid coolant coils in the evaporator 9 a liquid (e.g., water) represented by arrow 71. Similar to the embodiments of FIG. 1, a controller or processor—in this embodiment designated by the numeral 78—evaluates the measured temperature of air entering the condenser 3 and determines if an on/off duty cycle and what the duration of duty cycle periods should be, or if a continuous ON cycle should be employed in the coolant pump and motor 8 when the latter is otherwise normally powered on.

The embodiment shown in FIG. 4, operates similarly to that of FIG. 3 except that the controller or processor—in this embodiment designated by numeral 88—evaluates the measured temperature of the liquid coolant 71 via temperature sensor 87 and, like that of the system in FIG. 3, determines if an on/off duty cycle and its duration or if instead a continuous ON cycle should be employed on the pump and motor 8 when otherwise normally powered on.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A vapor compression thermal control system, comprising:
    at least one refrigerant, circuit having a compressor, a condenser, and an air-to-refrigerant evaporator and a refrigerant;
    at least one electrically powered evaporator air mover comprising one of a blower and fan; and
    an apparatus to prevent compressor overloading configured such that only temperature of indoor ambient air entering the evaporator from a space whose temperature is being controlled by the system is measured and compared with at least one predetermined temperature setting to determine that a state of compressor overloading is being reached, wherein when the measured temperature exceeds the predetermined temperature the apparatus is further configured to shut off and subsequently turn back on the evaporator air mover for time periods sufficient to reduce heat transfer in the evaporator.

2. The system according to claim 1, wherein the apparatus comprises at least one of a bi-metallic strip, a thermocouple, a resistance temperature transducer and a thermistor to measure the indoor ambient air temperature.

3. The system according to claim 1, wherein the apparatus comprises a microprocessor that compares the measured temperature with the at least one predetermined temperature setting.

4. A vapor compression thermal control system, comprising:
    at least one refrigerant circuit having a compressor, a condenser, an air-to-refrigerant evaporator and a refrigerant;
    at least one electrically powered evaporator air mover comprising one of a blower and fan; and
    an apparatus for preventing compressor overloading configured such that only temperature of outdoor ambient air being used to cool the condenser is measured and compared with at least one predetermined temperature setting to determine that a state of compressor overloading is being reached, wherein when the measured temperature exceeds the predetermined temperature the apparatus is further configured to shut off and subsequently turn back on the evaporator air mover for time periods sufficient to reduce heat transfer in the evaporator.

5. The system according to claim 4, wherein the apparatus comprises at least one of a bi-metallic strip, a thermocouple, a resistance temperature transducer and a thermistor to measure the outdoor ambient air temperature.

6. The system according to claim 4, wherein the apparatus comprises a microprocessor that compares the measured temperature with the at least one predetermined temperature setting.

7. In a vapor compression heat pump thermal control system, having at least one refrigerant circuit with a compressor, a condenser, an air-to-refrigerant evaporator, a refrigerant; and at least one electrically powered blower or fan configured to operate as an evaporator heat exchanger air mover, the improvement comprising
    an apparatus for preventing compressor overloading configured such that only temperature of ambient air being drawn into the indoor heat exchanger from a space whose temperature is being controlled by the system or into the outdoor heat exchanger from outdoor ambient air is measured and compared with at least one predetermined temperature setting to determine that a state of compressor overloading is being reached, wherein when the measured, temperature exceeds the predetermined temperature the apparatus is further configured to shut off and subsequently turn back on the heat exchanger air mover for time periods sufficient to reduce heat transfer in the evaporator.

8. The system according to claim 7, wherein the apparatus comprises at least one of a bi-metallic strip, a thermocouple, a resistance temperature transducer and a thermistor to measure the indoor or outdoor ambient air temperature, respectively.

9. The system according to claim 7, wherein the apparatus comprises a microprocessor that compares the measured temperature with the at least one predetermined temperature setting.

10. A vapor compression thermal control system, comprising:
    at least one refrigerant circuit having a compressor, a condenser, a liquid-to-refrigerant evaporator and a refrigerant;

at least one electrically powered evaporator liquid circulation pump; and an apparatus to prevent compressor overloading configured such that only temperature of coolant flowing from a space whose temperature is being controlled by the system and entering the evaporator is measured and compared with at least one predetermined temperature setting to determine that a state of compressor overloading is being reached, wherein when the measured temperature exceeds the predetermined temperature the apparatus is further configured to shut off and subsequently turn back on the evaporator pump for time periods sufficient to reduce heat transfer in the evaporator.

11. The system according to claim 10, wherein the apparatus comprises at least one of a bi-metallic strip, a thermocouple, a resistance temperature transducer and a thermistor to measure the coolant temperature.

12. The system according to claim 10, wherein the apparatus comprises a microprocessor that compares the measured temperature with the at least one predetermined temperature setting.

13. A vapor compression thermal control, system, comprising:

at least one refrigerant circuit having a compressor, a condenser, and a liquid-to-refrigerant evaporator and a refrigerant;

at least one electrically powered evaporator liquid circulation pump; and an apparatus for preventing compressor overloading configured such that only temperature of outside ambient air being used to cool the condenser is measured and compared with at least one predetermined temperature setting to determine that a state of compressor overloading is being reached, wherein when the measured temperature exceeds the predetermined temperature the apparatus is further configured to shut off and subsequently turn back on the evaporator pump for time periods sufficient to reduce heat transfer in the evaporator.

14. The system according to claim 13, wherein the apparatus comprises at least one of a bi-metallic strip, a thermocouple, a resistance temperature transducer and a thermistor to measure the outdoor ambient air temperature.

15. The system according to claim 13, wherein the apparatus comprises a microprocessor that compares the measured temperature with the at least one predetermined temperature setting.

* * * * *